US009655983B2

(12) United States Patent
Meyer et al.

(10) Patent No.: US 9,655,983 B2
(45) Date of Patent: May 23, 2017

(54) PROCESS FOR PREPARING A PHARMACEUTICAL FORMULATION OF CONTRAST AGENTS

(75) Inventors: Dominique Meyer, La Rochelle (FR); Claire Corot, Lyons (FR); Marc Port, Deuil la Barre (FR); Vincent Barbotin, Montmorency (FR); Bruno Bonnemain, Villeparisis (FR)

(73) Assignee: GUERBET, Villepinte (FR)

( * ) Notice: Subject to any disclaimer, the term of this patent is extended or adjusted under 35 U.S.C. 154(b) by 0 days.

(21) Appl. No.: 12/918,259

(22) PCT Filed: Feb. 18, 2009

(86) PCT No.: PCT/EP2009/051937
§ 371 (c)(1),
(2), (4) Date: Feb. 8, 2011

(87) PCT Pub. No.: WO2009/103744
PCT Pub. Date: Aug. 27, 2009

(65) Prior Publication Data
US 2011/0129425 A1 Jun. 2, 2011

Related U.S. Application Data

(63) Continuation of application No. 12/155,997, filed on Jun. 12, 2008, now abandoned.

(30) Foreign Application Priority Data

Feb. 19, 2008 (FR) ..................................... 08 51055
Apr. 17, 2008 (EP) ..................................... 08154745

(51) Int. Cl.
A61K 49/10 (2006.01)
A61K 45/06 (2006.01)
A61K 9/00 (2006.01)

(52) U.S. Cl.
CPC .......... *A61K 49/108* (2013.01); *A61K 9/0019* (2013.01); *A61K 45/06* (2013.01); *A61K 49/106* (2013.01)

(58) Field of Classification Search
None
See application file for complete search history.

(56) References Cited

U.S. PATENT DOCUMENTS

| | | | |
|---|---|---|---|
| 4,639,365 A | 1/1987 | Sherry | |
| 4,647,447 A | 3/1987 | Gries et al. | |
| 4,877,600 A | 10/1989 | Bonnemain et al. | |
| 5,049,667 A | 9/1991 | Schaefer et al. | |
| 5,082,649 A | 1/1992 | Vanderipe | |
| 5,098,692 A | 3/1992 | Gries et al. | |
| 5,362,475 A | 11/1994 | Gries et al. | |
| 5,364,613 A * | 11/1994 | Sieving et al. | 424/9.3 |
| 5,650,133 A | 7/1997 | Carvalho et al. | |
| 5,846,517 A * | 12/1998 | Unger | 424/9.52 |
| 5,876,695 A | 3/1999 | Gries et al. | |
| 5,958,373 A | 9/1999 | Garrity et al. | |
| 7,385,041 B2 | 6/2008 | Chang et al. | |
| 2003/0059368 A1* | 3/2003 | Groman et al. | 424/1.11 |
| 2004/0170566 A1 | 9/2004 | Chang et al. | |

FOREIGN PATENT DOCUMENTS

| | | |
|---|---|---|
| EP | 0 270 483 A2 | 6/1988 |
| EP | 0 481 526 A1 | 4/1992 |
| EP | 0 454 078 B1 | 10/1996 |
| FR | 2 590 484 A1 | 5/1987 |
| WO | WO 86/02352 A1 | 4/1986 |
| WO | WO 89/00052 A1 | 1/1989 |
| WO | WO 90/03804 A1 | 4/1990 |
| WO | WO 90/12050 A1 | 10/1990 |
| WO | WO 91/10645 A2 | 7/1991 |
| WO | WO 93/20852 A2 | 10/1993 |
| WO | WO 03/011115 A2 | 2/2003 |

(Continued)

OTHER PUBLICATIONS

Chang et al. Inorg Chem, 32, p. 3501-3508, 1993.*
Definition of "industrail process" from www.thefreedictionary.com, accessed Jun. 27, 2016.*
Desreux, J. F., and D. Gilsoul. "Chemical synthesis of paramagnetic complexes." Trends in contrast media. Springer Berlin Heidelberg, 1999. 161-168.*
"Nephrogenic Systemic Fibrosis: An Uncommon and Debilitating Disease Possibly Associated with Gadolinium Chelates", Guerbet Contrast for Life, Information for Healthcare Professionals and Investors, (online), Dec. 21, 2007, pp. 1-7, XP002499276.

(Continued)

*Primary Examiner* — Nissa Westerberg
(74) *Attorney, Agent, or Firm* — Birch, Stewart, Kolasch & Birch, LLP

(57) ABSTRACT

The invention relates to a process for preparing a liquid pharmaceutical formulation containing a complex of macrocyclic chelate with a lanthanide and a mol/mol amount of free macrocyclic chelate of between 0.002% and 0.4%, advantageously between 0.02% and 0.3% and very advantageously between 0.025% and 0.25%, the macrocyclic chelate advantageously being chosen from DOTA, NOTA, DOTAGA, DO3A, BT-DO3A, HP-DO3A and PCTA, and is preferably DOTA, the said process comprising the following successive steps: b) preparation of a liquid pharmaceutical composition containing, firstly, the complex of macrocyclic chelate with a lanthanide, and, secondly, free macrocyclic chelate and/or free lanthanide; c) measurement in the pharmaceutical formulation obtained in step b) of the concentration of free macrocyclic chelate C ch1 and/or of free lanthanide C lan1; d) adjustment of C ch1 and/or of C lan1 so as to obtain C ch1=C tch1 and C lan1=0, wherein C t ch1 is the target concentration of free macrocyclic chelate in the final liquid pharmaceutical formulation.

14 Claims, No Drawings

(56) References Cited

FOREIGN PATENT DOCUMENTS

| WO | WO 2004/013161 A2 | 2/2004 |
|---|---|---|
| WO | WO 2007/002109 A2 | 1/2007 |
| WO | WO 2007/042504 A2 | 4/2007 |
| WO | WO 2007/106544 A2 | 9/2007 |
| WO | WO 2007/121453 A2 | 10/2007 |

OTHER PUBLICATIONS

"Stability of linear and macrocyclic gadolinium based contrast agents", The British Journal of Radiology, vol. 80, pp. 581-585, 2007.
"'Stability'" of gadolinium chelates, The British Journal of Radiology, pp. 583-584, Jul. 2007.
Author's reply, The British Journal of Radiology, Correspondence, pp. 584-585, Jul. 2007.
Berlex Canada Inc., Product Monograph of Gadovist® 1.0 "Contrast Enhancement Agent for Magnetic Resonance Imaging (MRI)", Oct. 22, 1999.
Bousquet et al, "Gd-DOTA: Characterization of a New Paramagnetic Complex1", Contrast Media, Radiology, vol. 166, pp. 693-698, 1988.
Bracco Diagnostics, Inc., ProHance® Multipack™ (Gadoteridol) Injection, p. 1, Revised Apr. 2006.
Cabella et al., "Cellular labeling with Gd(III) chelates: only high thermodynamic stabilities prevent the cells acting as 'sponges' of Gd3+ ions", Contrast Media & Molecular Imaging, vol. 1, pp. 23-29, 2006.
Caravan et al., "Gadolinium(III) Chelates as MRI Contrast Agents: Structure, Dynamics, and Applications", Chemical Rev., vol. 99, pp. 2293-2352, 1999.
Corot et al., "Structure-Activity Relationship of Macrocyclic and Linear Gadolinium Chelates: Investigation of Transmetallation Effect on the Zinc-Dependent Metallopeptidase Angiotensin-Converting Enzyme", Journal of Magnetic Resonance Imaging, vol. 8, No. 3, pp. 695-702, May 1, 1998, XP008097347.
Dunand et al., "How Does Internal Motion Influence the Relaxation of the Water Protons in LnIIIDOTA-like Complexes?", Journal of American Chemical Society, vol. 124, No. 4, pp. 710-716, 2002.
Ersoy et al., "Biochemical Safety Profiles of Gadolinium-Based Extracellular Contrast Agents and Nephrogenic Systemic Fibrosis", Journal of Magnetic Resonance Imaging, vol. 26, pp. 1190-1197, 2007.
Guerbet Company Contrast for Life, Description of Product Dotarem®, Apr. 2007.
Idée et al., "Clinical and biological consequences of transmetallation induced by contrast agents for magnetic resonance imaging: a review", Fundamental & Clinical Pharmacology, vol. 20, No. 6, pp. 563-576, 2006, XP002549063.
International Search Report dated Apr. 11, 2009 for Application No. PCT/EP2009/051937.
Kimura et al., "Human Comparative Study of Zinc and Copper Excretion via Urine after Adminstration of Magnetic Resonance Imaging Contrast Agents", Radiation Medicine-Medical Imaging and Radiation Oncology, vol. 23, No. 5, pp. 322-326, Aug. 2005, XP002499275.
Kumar et al., "Synthesis, Stability, and Structure of Gadolinium(III) and Yttrium(III) Macrocyclic Poly(amino carboxylates)", Inorganic Chemistry, vol. 33, pp. 3567-3575, 1994.
Laurent et al., "Comparative study of the physicochemical properties of six clinical low molecular weight gadolinium contrast agents", Contrast Media & Molecular Imaging, vol. 1, pp. 128-137, 2006.
Magnevist® (brand of gadopentetate dimeglumine) Injection, description of product, 6061806, May 2007.
Moreau et al., "Complexing Mechanism of the Lanthanide Cations Eu3+, Gd3+, and Tb3+ with 1,4,7,10-Tetrakis (carboxymethyl)-1,4,7,10-tetraazacyclododecane (dota)-Characterization of Three Successive Complexing Phases: . . . EXAFS", Chem. Eur. J., vol. 10, pp. 5218-5232, 2004.

Penfield, "Nephrogenic systemic fibrosis and the use of gadolinium-based contrast agents", Pediatr Nephrol, vol. 23, pp. 2121-2129, 2008.
Port et al., "Efficiency, thermodynamic and kinetic stability of marketed gadolinium chelates and their possible clinical consequences: a critical review", Biometals, vol. 21, pp. 469-490, 2008.
Preliminary Search Report dated Oct. 13, 2008 for French Application No. 0851055.
Thomsen, "Nephrogenic Systemic Fibrosis", Imaging Decisions, pp. 13-18, Apr. 2007.
Tweedle, "Physicochemical Properties of Gadoteridol and Other Magnetic Resonance Contrast Agents", Investigative Radiology, vol. 27, S2-S6, 1992.
Wang et al., "A Kinetic Investigation of the Lanthanide DOTA Chelates. Stability and Rates of Formation and of Dissociation of a Macrocyclic Gadolinium(III) Polyaza Polycarboxylic MRI Contrast Agent", Inorganic Chemistry, vol. 31, No. 6, pp. 1095-1099, 1992.
White et al., "Comparison of Gd (DTPA-BMA) (Omniscan) Versus Gd (HP-DO3A) (ProHance) Relative to Gadolinium Retention in Human Bone Tissue by Inductively Coupled Plasma Mass Spectroscopy", Investigative Radiology, vol. 41, No. 3, pp. 272-278, Mar. 2006.
Zhu et al., "Formation kinetics and stability studies on the lanthanide complexes of 1,4,7,10-tetra-azacyclododecane-N,N',N'',N'''-tetraacetic acid by capillary electrophoresis", Electrophoresis 2002, vol. 23, No. 9, pp. 1348-1356, XP008097346.
AFSSAPS, "DOTAREM 0.5 mmol/ml solution for injection in pre-filled syringe," Feb. 1995, 2 pages.
AFSSAPS, "DOTAREM 0.5 mmol/ml solution for injection," Mar. 1989, 2 pages.
Guerbet, "DOTAREM 0.5 mmol/ml, solution for injection," Cedex, France, Jun. 2007, 2 pages.
Guerbet, "Guerbet 2008 first-half sales highlights," Jul. 29, 2008, Villepinte, France, 1 page.
USP-NF, Second Supplement, U.S. Pharmacopeia and National Formulary, Aug. 1, 2004, pp. 3227, 3257-3259.
"A Guideline on Summary of Product Characteristics (SmPC)", Revision 2, Sep. 2009.
"Excipients in the label and package leaflet of medicinal products for human use", vol. 3B, Guidlines: Medicinal products for human use safety, environment and information, Jul. 2003.
Delgado, R. et al., "Metal Complexes of Cyclic Tetra-Azatetra-Acetic Acids", Talanta, vol. 29, pp. 815-822, 1982.
Granger et al., "Successful Treatment of Cervical Spinal Epidural Empyema Secondary to Grass Awn Migration in a Cat", Journal of Feline Medicine and Surgery, vol. 9, pp. 340-345, 2007.
"MRI ContrastAgent", Pharmacia, vol. 37, No. 5, 2001, pp. 420-421 with English language translation.
"Nephrogenic Systemic Fibrosis: An uncommon and Debilitating Disease Possibly Associated with Gadolinum Chelates", Information for Healthcare Professionals and other Stakeholders, dated Jul. 2, 2008.
Minutes of the Oral Proceedings for EP Application No. 09 712 403.6-1453 dated Oct. 21, 2013.
Declaration of Mag. Dr. Raffael Schuecker concerning Example 17 of WO 91/10645 dated Nov. 3, 2014.
Declaration of Stefan Welzig, Ph.D., concerning the reproduction of Example 2 of EP 2 242 515, dated Dec. 16, 2014.
Desreux, J.F., "Nuclear Magnetic Resonance Spectroscopy of Lanthanide Complexes with a Tetraacetic Tetraaza Macrocycle. Unusual Conformation Properties", Inorg. Chem., vol. 19, 1980, pp. 1319-1324.
European Pharmacopoeia 5.0, 01/2005:10100, pp. 5, 2692-2693.
Kirchin et al., "Contrast Agents for Magnetic Resonance Imaging: Safety Update", Topics in Magnetic Resonance Imaging, vol. 14, No. 5, Oct. 2003, pp. 426-435.
Kuo, Phillip H., "Gaolinium-Containing MRI Contrast Agents: Important Variations on a Theme for NSF", J. of the American College of Radiology, vol. 5, No. 1, 2008, pp. 29-35.
Micard et al., "Stability and Sterility of Meglumine Gadoterate Injection Repackaged in Plastic Syringes", International J. of Pharmaceutics, vol. 212, 2001, pp. 93-99.

(56) References Cited

OTHER PUBLICATIONS

Schaefer, Michel, "Properties of Paramagnetic Metals in MRI", Metal-based Drugs vol. 4, No. 3, 1997, pp. 159-171.
Supplemental Experimental Data: To Demonstrate the Importance of the Adjustment Step in the Process. Faxed May 8, 2013.
Technical Report 8502, "The Field Production of Water for Injection", US Army Medical Bioengineering Research and Development Laboratory, Dec. 1983, pp. 58-59, 83.
Wu et al., "Kinetics of Formation of Ca2+ Complexes of Acyclic and Macrocyclic Poly(amino carboxylate) Ligands: Bimolecular Rate Constants for the Fully-Deprotonated Ligands Reveal the Effect of Macrocyclic Ligand Constraints on the Rate Determining . . . ", Inorg. Chem. vol. 36, 1997, pp. 1884-1889.
Affidavit by Dr. Philipp Welbergen dated Feb. 19, 2015.
Affidavit by Klaus-Dieter Schade dated Feb. 19, 2015.
Affidavit by Stefaan Lingier dated Feb. 19, 2015.
Delivery notes from curagita of vials Dotarem 0.5 mmol/ml dated Dec. 12, 2007 and Dec. 19, 2007.
Keuren Marijke, "Analysis Report of the determination of Ca-level", Research & Development Materials, Dec. 10, 2014.
L. Van de Voorde, "Analysis Report of the determination of the concentration of free DOTA", Research & Development Materials, Feb. 16, 2015.
Leaflet supplied together with the 20 ml vial DOTAREM 0.5 mmol/ml with batch No. 07GD050A, Dated Dec. 10, 2014.
Medical Imaging Drugs Advisory Committee, presented on Feb. 14, 2013, p. 9, http://www.fda.gov/downloads/AdvisoryCommittees/CommitteesMeetingMaterials/Drugs/MedicalImagingl.
Silvio Aime et al., "Synthesis, Characterization, and 1/T1 NMRD Profiles of Gadolinium(III) Complexes of Monoamide Derivatives of DOTA-like Ligands . . . ", Inorganic Chemistry, vol. 31, No. 12, pp. 2422-2428, 1992.
Barge et al, "How to determine free Gd and free ligand in solution of Gd chelates. A technical note," Contrast Media and Molecular Imaging, vol. 1, 2006 (Published online Sep. 28, 2006), pp. 184-188.
CDER, "Guidance for Industry PAT—A Framework for Innovative Pharmaceutical Development, Manufacturing, and Quality Assurance," FDA, Sep. 2004, pp. 1-16 (19 pages).
Declaration by Dr. Thomas Frenzel, concerning Example 17 of WO 91/10645, 3 pages, date unknown.
Declaration by Dr. Thomas Frenzel, concerning Example 2 in US 5 876 695 and in EP 2 242 515, 3 pages, dated May 31, 2016.
Declaration by Prof. F. Ekkehardt Hahn, concerning the formation of Gd-DOTA complexes, 1 page, dated Apr. 26, 2016.
European Communication, dated Feb. 8, 2016, for European Application No. 14165006.9.
Gries, "Extracellular MRI Contrast Agents Based on Gadolinium," Topics in Current Chemistry, vol. 221, 2002, pp. 1-24.
Hagan et al, "Fluorescence Detection of Gadolinium Chelates Separated by Reversed-Phase High-Performance Liquid Chromatography," Analytical Chemistry, vol. 60, No. 6, Mar. 15, 1988, pp. 514-516.
Meier et al., "Report regarding the synthesis of Gd-DOTA according to Patent EP 2 242 515 B1," pp. 1-4 (14 pages), date unknown.
Supplemental Data: Repetition of Example 2 in EP 2 242 515 at the industrial scale, 3 pages, date unknown.
Watson et al, "Contrast Agents" Chapter 14, pp. 372-385, 1992.
FDA, "Prescribing information" of Dotarem, Reference ID: 3279681, 2013, 25 pages.
Guerbet, "Dotarem® Injection," Feb. 14, 2013, pp. CI-1-CI-9.
Parizel et al., "Gadolinium-DOTA Enhanced MR Imaging of Intracranial Lesions," J. Computer Assisted Tomography, May/Jun. 1989, vol. 13, No. 3, pp. 378-385.
Peyroux, "Dotarem®," Guerbet, Feb. 2005, 2 pages.
Tóth et al., "Kinetics of Formation and Dissociation of Lanthanide(III)-DOTA Complexes," Inorganic Chemistry, vol. 33, No. 18, 1994, pp. 4070-4076.
Weinmann et al., "Gadolinium Chelates: Chemistry, Safety, and Behavior," Encyclopedia of Magnetic Resonance, 2007, pp. 1-8.
English language translation of Vidal, ISBN 2-85091-092-9, MAGNEVIST Gadopentetic acid, 2002 (7pages).
Kumar et al., "Macrocyclic polyaminocarboxylate complexes of lanthanides as magnetic resonance imaging contrast agents," Pure & Appl. Chem., vol. 65, No. 3, 1993, pp. 515-520.
Meyer et al., "Gd-DOTA, A Potential MRI Contrast Agent Current Status of Physicochemical Knowledge," Investigative Radiology, vol. 23, No. 9, 1988, pp. S232-S235.
Moi et al., "Stable Bifunctional Chelates of Metals Used in Radiotherapy," Cancer Research (Suppl.), vol. 50, 1990, pp. 789s-793s.
Frenzel et al., "Stability of Gadolinium-Based Magnetic Resonance Imaging Contrast Agents in Human Serum at 37°C," Investigative Radiology, vol. 43, No. 12, Dec. 2008, pp. 817-828.

* cited by examiner

PROCESS FOR PREPARING A PHARMACEUTICAL FORMULATION OF CONTRAST AGENTS

This application is the National Phase of PCT/EP2009/051937 filed on Feb. 18, 2009, which claims priority under 35 U.S.C. 119(a) to Patent Application Nos. 0851055 and 08154745.7 filed in France on Feb. 19, 2008 and European Patent Office on Apr. 17, 2008, respectively, and claims the benefit of U.S. application Ser. No. 12/155,997, filed on Jun. 12, 2008, all of which are hereby expressly incorporated by reference into the present application.

The invention relates to pharmaceutical formulations of contrast agents, in particular of complexes of chelates with paramagnetic metal ions, especially for magnetic resonance imaging, and to industrially efficient processes for obtaining these formulations.

Many contrast agents based on complexes of chelates with lanthanides (paramagnetic metal), in particular with gadolinium, are known, and are described, for example, in document U.S. Pat. No. 4,647,447. Several products are marketed, especially based on macrocyclic chelates such as DOTA gadoterate (1,4,7,10-tetraazacyclo-dodecane-N,N', N'',N'''-tetraacetic acid) and gadoteridol HPDO3A, and linear chelates such as DTPA (diethylenetriaminepentaacetic acid) and DTPA-BMA (gadodiamide).

In the body, the complexes of chelates with lanthanide are in a situation of chemical equilibrium, which may lead to a risk of undesired release of the lanthanide, and more especially of gadolinium. A person skilled in the art is thus led to seek technical solutions that limit this risk in order to solve the complex problem of tolerance in the patient as safely as possible. This problem is all the more difficult since the administration of contrast agents is often repeated during diagnostic examinations and/or for the guiding and monitoring of the efficacy of a therapeutic treatment.

Several approaches for improving the tolerance of complexes of chelates with gadolinium are described in the prior art.

More than twenty years ago (U.S. Pat. No. 5,876,695), those skilled in the art were working on formulations consisting of the addition to a lanthanide-complexing chelate of an amount of chelate in excess, i.e. chelate non-complexed by the lanthanide. This excess chelate is intended to compensate for an undesired release of lanthanide, the excess chelate then complexing with the released lanthanide ($Gd^{3+}$ metal ion).

In U.S. Pat. No. 5,876,695 the chelates (ligands L) added in excess for macrocyclic chelates are described under the form of an excipient having the formula X[X',L], where X and X' are metal ions (especially calcium, sodium, zinc or magnesium) and L is the chelate in excess. These excipients are designed to scavenge free lanthanide.

For instance for the chelate DOTA, an excipient is Na2[Ca-DOTA]: the DOTA chelate in excess is complexed by the calcium ion Ca2+ in the cage formed by the chelate, with a resulting charge 2+ to be neutralised by two Na+ ions.

A few years later, an improvement of these excipients X[X',L] was presented in the patent EP 454 078 (U.S. Pat. No. 7,385,041) with improved X[X',L] where both X and X' are calcium or zinc, these excipients being able even at low dosage (0.1% mol/mol) to scavenge both free lanthanide and free organic ligand chelate. This document covers these excipients, in particular for example the calcium salts of calcium chelated complex, notably Ca[Ca-HPDO3A]$_2$ instead of Na[Ca-HPDO3A], and explains (in detail notably column 1 lines 21-40) that a free macrocyclic ligand L instead of such excipient X[X',L] should not be used for safety reasons due to the toxicity of free chelate L.

In particular, table 1 of U.S. Pat. No. 7,385,041 illustrates with LD50 values that free macrocyclics chelates (HP-DO3A, DO3A, DOTA) are about at least 10 times more toxic than these macrocycles under the form X[X',L]. In particular for DOTA, the LD50 is at least about 40 times better for Na2[Ca-DOTA] than for free DOTA.

|   | Chelate | Letal dose (LD 50) mMol/Kg |
|---|---|---|
| Free macrocyclic chelate L (not used as excess ligand) | HP-DO3A | 0.11 |
|   | DO3A | 0.12 |
|   | DOTA | 0.18 |
| Excipient X[X', L] | Ca[Ca-HPDO3A]$_2$ | 1.3 |
|   | Ca[Ca-DO3A]$_2$. | 1.6 |
|   | Na2 [Ca-DOTA] | >7 |
| Chelate-Gd | DOTA-Gd | 14 |
|   | HP-DO3A-Gd | 12 |

The formulation of the commercialised product gadoteridol (Prohance Bracco) includes 0.1% Ca[Ca-HPDO3A]$_2$, and gadobutrol product (Gadovist Bayer Schering) includes Na[Ca-BT DO3A] excipient.

As a conclusion, no document of the prior art describes that the formulation of a macrocyclic chelate administered to the patient contains or should contain, besides the macrocyclic chelate complexed by the lanthanide, an excess of free macrocyclic chelate (in a specific and low range) that is under the form of a free chelate L which was not complexed with any metal ions and in particular that is not under the form of an excipient X[X',L]. On the opposite the one skilled in the art was discouraged to do so due to a risk in terms of tolerance of free macrocyclic chelate.

It is also emphasized that in the prior art for the macrocyclic chelate (contrarily to the invention as described later), the dedicated excipient X[X',L] was added after the complexation of the chelate by the lanthanide (see the numerous examples of U.S. Pat. No. 5,876,695 and U.S. Pat. No. 7,385,041). The complexation was realised according to the steochiometric proportions of the chelate L (HP-DO3A for example) and lanthanide "lan" (Gd3+ for example). Following scheme I describes the manufacturing process of the prior art (sp means steochiometric proportions):

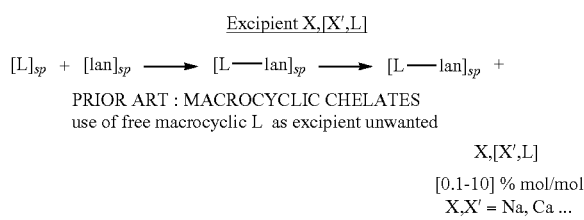

PRIOR ART : MACROCYCLIC CHELATES
use of free macrocyclic L as excipient unwanted X,[X',L]
[0.1-10] % mol/mol
X,X' = Na, Ca ...

Despite all these prior-art studies, the complex problem of tolerance still exists, especially in situations at risk of more pronounced tolerance for the administration of MRI contrast products. For instance a very different approach was tested recently as illustrated in WO 2007/106 544 with grafting onto the chelates chemical groups intended to increase the affinity of the chelate for the metal.

A new problem has moreover recently appeared in the matter of tolerance, namely a pathology known as NSF (nephrologic systemic fibrosis, or fibrogenic dermopathy, with very severe effects on human skin), which may be at least partly correlated to the existence of free gadolinium, i.e. non-complexed gadolinium, in the body. This disease has led to health authorities being alerted as regards certain categories of patients with respect to marketed gadolinium-based contrast agents. Briefly, NSF could be associated to the transmetallation of some lanthanide from the complex [lanthanide-chelate] by endogenic ions such as zinc and resulting in unwanted release of free lanthanide.

In summary, this problem of tolerance of complexes of chelates with lanthanides remains complex and important, leading to the research of even more safe products, and to the necessity of a perfectly controlled rate of the different entities in the pharmaceutical solutions.

The Applicant has worked on the specific case of macrocyclic chelates, and has demonstrated, contrary to what was expected, the very satisfying tolerance obtained when using an amount of excess free macrocyclic chelate at a particular low dose range, and not under the form of an excipient X[X',L] of the prior art.

The Applicant has shown that with macrocyclic chelates, and in particular DOTA, results are very advantageous, using a very low excess of free chelate L, so that the pharmaceutical composition administered to the patient contains more specifically between 0.02% and 0.4% and in particular between 0.025% and 0.25% of the free macrocyclic chelate L.

For the purposes of the present invention hereafter, the term "free macrocyclic chelate" means any macrocyclic chelate L not complexed with lanthanide or with other metal ions, and in particular not under the form of an excipient X[X',L] in which X and X' are as described above.

Briefly the formulation selected by the Applicant with free macrocycle has the strong advantage, notably in view of the NSF, of increasing highly the scavenging capacity of potential free gadolinium, as compared to the prior excipients X[X',L], as explained further in detail in the application.

Consequently, in view of this low amount of free excess, a new problem arises, which is unknown in the prior art, namely the need for extremely precise and delicate industrial-scale control of the concentrations of free macrocyclic chelate and thus of the manufacture of the product to arrive at this range of target values of amount of free chelate, these values needing to be stable, including after storage for several months or years.

Specifically, taking into account the production volumes, which are of the order of several tens of tons of active principle, the Applicant had to develop a new and particularly optimised preparation process that makes it possible to ensure the reliability and reproducibility of the composition of commercialized batches.

In particular, the Applicant found that the mixing of stoichiometric amounts on the basis of the theoretical calculation does not sufficiently satisfactorily give at the industrial scale the respective amounts of complex of chelate with the lanthanide and of free chelate in low concentration in the pharmaceutical formulation. The reason for this is that it is then necessary to perform several analysis steps, which takes several hours, and significantly increases the industrial cost price of the product. In contrast, the Applicant's process makes it possible especially to prepare beforehand and to optimize the analytical device, which is important as regards its impact on the quality of the final product.

More specifically, by respecting the stoichiometric proportions and by adding an excess of DOTA intended not to be complexed with the lanthanide, it is not possible at the industrial scale to achieve sufficiently reproducibly in the final pharmaceutical solution an excess of free DOTA in the target range, especially given:

1) the uncertainty of weighing at the industrial scale, which does not make it possible to correctly ensure the ratio (of the order of 1000) between the chelate and the excess chelate, given the small amount of excess chelate;

2) the variability of the hygroscopic characteristics of the chelate (associated with its acid functions).

It is pointed out, specifically, that to prepare an industrial amount, typically, for example 200 liters of a 0.5 M solution of gadolinium chelate (for example DOTA-Gd), the amount of DOTA to be added in excess after complexation of the DOTA with the lanthanide, to obtain an excess of free DOTA of 0.1 mol/mol %, would be about 40 g of DOTA in 200 liters of the DOTA solution (40 g in addition to the 40 kg of DOTA initially placed in solution), which does not allow sufficiently reliable reproducibility at the industrial level.

This problem has been solved by the Applicant by means of using at least one step of measuring in the liquid pharmaceutical formulation concentrations of free macrocyclic chelate ($C_{ch\ 1}$) and/or of free lanthanide ($C_{lan\ 1}$) and at least one step of adjusting the $C_{ch\ 1}$ and/or the $C_{lan\ 1}$ so as to obtain the desired concentration of $C_{ch\ 1}$ and $C_{lan\ 1}=0$, advantageously by modifying the amounts of macrocyclic chelate or of lanthanide in the pharmaceutical composition.

$C_{ch\ 1}$ abbreviation refers to the concentration of free chelate.

$C_{lan\ 1}$ abbreviation refers to the concentration of free lanthanide.

Throughout the application, the equality $C_{lan\ 1}=0$ is used to define that $C_{lan\ 1}$ in the formulation injected into the patient is zero or substantially zero (typically less than $10^{-10}$ M and advantageously less than $10^{-12}$ M or $10^{-14}$ M), the possible presence in solution of an extremely small amount of lanthanide not being able to be totally excluded. The reason for this is that concentrations less than $10^{-10}$ M cannot be measured sufficiently reliably by the current analytical methods.

Thus, according to one aspect, the present invention relates to a process for preparing a liquid pharmaceutical formulation of complex of macrocyclic chelate with lanthanide, the said process comprising at least one step of measuring in the liquid pharmaceutical formulation concentrations of free macrocyclic chelate ($C_{ch\ 1}$) and/or of free lanthanide ($C_{lan\ 1}$) and at least one step of adjusting the $C_{ch\ 1}$ and/or the $C_{lan\ 1}$, so as to obtain (sufficiently stably in the final pharmaceutical solution, i.e. the pharmaceutical formulation intended to be administered to the patient) a mol/mol amount of free macrocyclic chelate of between 0.002% and 0.4%, advantageously between 0.02% and 0.3% and very advantageously between 0.025% and 0.25%.

The present invention thus relates to a process for preparing a liquid pharmaceutical formulation containing a complex of macrocyclic chelate with a lanthanide and a mol/mol amount of free macrocyclic chelate of between 0.002% and 0.4%, advantageously between 0.02% and 0.3% and very advantageously between 0.025% and 0.25%, the macrocyclic chelate advantageously being chosen from DOTA, NOTA, DOTAGA, DO3A, BT-DO3A (gadobutrol), HP-DO3A and PCTA, and is advantageously DOTA, the said process comprising the following successive steps:

b) preparation of a liquid pharmaceutical composition containing, firstly, the complex of macrocyclic chelate, with a lanthanide, and, secondly, free macrocyclic chelate, advantageously that is not under the form of an excipient X[X',L] in which L is the macrocyclic chelate and X and X' are a metal ion, in particular chosen independently from calcium, sodium, zinc and magnesium, and/or free lanthanide;

c) measurement in the pharmaceutical formulation obtained in step b) of the concentration of free macrocyclic chelate $C_{ch\ 1}$ and/or of free lanthanide $C_{lan\ 1}$;

d) adjustment of $C_{ch\ 1}$ and/or of $C_{lan\ 1}$ so as to obtain $C_{ch\ 1} = C_{t\ ch\ 1}$ and $C_{lan\ 1} = 0$, wherein $C_{t\ ch\ 1}$ is the target concentration of the free macrocyclic chelate in the final liquid pharmaceutical formulation.

Advantageously, the process according to the present invention comprises a prior step a) of determination of the theoretical target concentration of free macrocyclic chelate $C_{t\ ch\ 1}$ in the final liquid pharmaceutical formulation.

The reaction is represented as follows as Scheme II (with "L" the ligand chelate, and "lan" the lanthanide gadolinium Gd3+ for example):

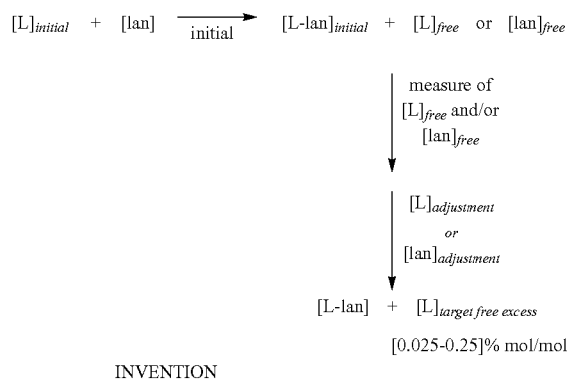

INVENTION

The reaction is in two steps:
Step 1:
$[L]_{initial} + [lan]_{initial} \rightarrow [L\text{-}lan] + [L]_{free}$ or $[lan]_{free}$ with the concentration $C_{ch\ 1}$ of $[L]_{free}$ and the concentration $C_{lan\ 1}$ of $[lan]_{free}$ being measured
Step 2:
$[L\text{-}lan]_{initial} + [L]_{free}$ or $[lan]_{free} + [L]_{adjustment}$ or $[lan]_{adjustment} \rightarrow [L\text{-}lan] + [L]_{target\ free}$ with the concentration $C_{ch\ 1} = C_{t\ ch\ 1}$ of $[L]_{target\ free}$ and $C_{lan\ 1} = 0$ of $[lan]_{free}$ For the purposes of the present invention, the term "amount of free macrocyclic chelate" means the proportion of free macrocyclic chelate relative to the amount of complexed macrocyclic chelate (gadoteric acid in the case of DOTA-Gd) present in the formulation in mol/mol. In the rest of the description, it will be referred to without preference as the "amount of free macrocyclic chelate" or the "excess free macrocyclic chelate". And as mentioned before, macrocyclic chelate L is not under the form of an excipient X[X',L] and is not complexed with any metal ion (namely X and X').

For the purposes of the present invention, the term "free lanthanide" means any lanthanide not complexed with a macrocyclic chelate.

It is recalled herein that in document U.S. Pat. No. 5,876,695 for the linear DTPA chelate, in Example 2, the amounts of excess chelate are defined from the start on the calculated basis of the stoichiometry, and without a step of prior adjustment or measurement of the concentrations. More specifically, in the said example, 0.5 mol of DTPA and 0.25 mol of gadolinium oxide ($Gd_2O_3$) are mixed in accordance with the stoichiometric proportions, and a 0.1 mol/mol % (0.5 mmol) excess of ligand is added; for macrocyclic chelates this does not ensure the target amount of ligand desired by the Applicant in the case of a large-scale industrial manufacture.

It is precised that the use of an excess of free linear ligand DTPA is destinated to scavenge free lanthanide that would otherwise be liberated during the conservation time of the formulation.

The adjustment process of the invention for macrocyclics is advantageously destinated to make absolutely sure (in particular due to the quantities used and to the detection limited capacities of the available analytical tools) that the level of free entities is totally controlled, and in particular that there is no free gadolinium in the manufactured pharmaceutical solution. This adjustment method is particularly advantageous for the industrial complexation issued from the mixture of the chelate and the lanthanide in solution.

It is also reminded that, as know by the one skilled in the art, the process of adjustment of the Applicant would not be applicable at the industrial scale with an excipient X[X',L] in view of the thermodynamic and kinetic equilibrium of such excipient, except maybe if further very complex methods were used (the manufacturer would have to manage both the metal ions and the lanthanide kinetic and thermodynamic constants).

As device for analysis/assay of the free macrocyclic chelate, any suitable equipment is used. Advantageously, a potentiometer or capillary electrophoresis is used for the macrocyclic chelate. More specifically, in the presence of copper sulfate, the free DOTA contained in the solution obtained from the complexation step (in bulk) complexes the copper. The excess copper sulfate is assayed in preferably pH 5 buffered medium, by potentiometry, with a solution of EDTA in the presence of a copper-indicating electrode and a reference electrode.

The analysis/assay of the free lanthanide is performed by using, for example, a solution of EDTA in the presence of xylenol orange Arsenezo as turning-point indicator. Free gadolinium is assayed advantageously with a colorimetric method using 0.01 M edetate disodium titration solution in the presence of xylenol orange as indicator. Titration is carried out in pH=5 sodium acetate/acetic acid buffered solution on 20 mL of DOTAREM product until the indicator turns colour from red to yellow. 0.1 ml of 0.01 M edetate disodium solution corresponds to 0.0008% weight/volume of free Gd (8 ppm). The method is valid from 8 to 100 ppm of free gadolinium To the knowledge of the Applicant colorimetric methods are well known but it was neither known nor suggested to use them for the measure of gadolinium Gd3+ in contrast agents at the very low levels of the present invention, which is of strong interest for the adjustment process of the invention and belongs to the same inventive concept. As such the invention also relates according to another aspect to an analytical method of measuring free lanthanide at the low range of the application and consisting in a colorimetric method (also called potentiometric method).

The present invention concerns an analytical colorimetric method for measuring the level of free lanthanide in a liquid pharmaceutical formulation containing a complex of macrocyclic chelate with a lanthanide and a mol/mol amount of free macrocyclic chelate of between 0.002% and 0.4%.

In order to perform step d), several solutions are possible as a function of the $C_{lan\ 1}$ and $C_{ch\ 1}$ measured in step c).

In particular, the following solutions are concerned:
if $C_{lan\ 1} > 0$ and/or $C_{ch\ 1} < C_{t\ ch\ 1}$, the adjustment may advantageously be performed by adding free macrocyclic chelate and/or by eliminating free lanthanide and/or by modifying the pH as described herein below;

if $C_{lan\ 1}=0$ and $C_{ch\ 1}>C_{t\ ch\ 1}$, the adjustment may advantageously be performed by eliminating free macrocyclic chelate and/or by adding free lanthanide and/or by modifying the pH as described hereinbelow.

In the situation of an elimination of free lanthanide, $[lan]_{adjustment}$ of Scheme 2 means that free lanthanide lan is eliminated.

In the situation of an elimination of free chelate, $[L]_{adjustment}$ of Scheme 2 means that free chelate L is eliminated.

Advantageously, the elimination of free lanthanide is performed by passing through an ion-exchange resin. It is thus possible, for example, to use a resin of styrene/divinylbenzene copolymers which contains iminodiacetate ions acting as chelating group for the binding with the metal ions ($Gd^{3+}$ in particular).

Advantageously, the elimination of free macrocyclic chelate is performed, for example, by filtration, advantageously using resins (for example anionic resins).

In one particular embodiment, step b) consists in mixing a solution of free macrocyclic chelate (initial) and of free lanthanide (initial) so as to obtain complexation of the lanthanide by the macrocyclic chelate, advantageously by adding the lanthanide (preferably solid lanthanide) into the solution of free macrocyclic chelate. It is emphasized that the prior art did not suggest that the optimisation of the complexation (so as to reach the target quantity of free excess ligand) would require the adjustment method of the Applicant.

The lanthanide is advantageously added in the form of oxide (gadolinium oxide in particular), but the invention also covers other possible forms of lanthanide, especially the lanthanide salts known to those skilled in the art.

The precise experimental conditions of step b) are detailed in the examples. Advantageously, the temperature for step b) is between 60 and 100° C., and is advantageously about 80° C. Advantageously, the pharmaceutical formulation is then cooled before the adjustment step d). The duration of step b) is, for example, from 1 hour to 3 hours.

Moreover, throughout the description hereinabove and hereinbelow of the adjustment variants of step d), it is understood that the complexation step b) may be performed in several sub-steps which would be equivalent to an overall complexation step. The complexation may be performed, for example, by preparing about half the final volume of the tank, and then adding gadolinium oxide at acidic pH.

It is possible to use a preparation process such that:
in step b), the amounts of free macrocyclic chelate (initial) and of free lanthanide (initial) added are equal to the stoichiometric proportions;
step c) consists in measuring $C_{ch\ 1}$ and/or $C_{lan\ 1}$;
step d) consists in adding to the formulation obtained in step b) the amount of free macrocyclic chelate necessary, firstly, to complete, if necessary the complexation of the free lanthanide and to obtain $C_{lan\ 1}=0$ (or substantially equal to 0), and, secondly, to obtain $C_{ch\ 1}=C_{t\ ch\ 1}$.

For the purposes of the present invention, the expression "the amounts of free macrocyclic chelate and of free lanthanide added are equal to the stoichiometric proportions" means that the amounts added are such that, in the light of the stoichiometry of the complexation reaction, all the lanthanide and all the chelate should be in complex form and there should be no free macrocyclic chelate.

However, advantageously, it is preferred, in the process according to the invention, for step c) of measurement of the concentrations to be performed in a medium in which the complexation reaction of step b) is performed:
by using a difference between the stoichiometric proportions and the amounts of free lanthanide and of free macrocyclic chelate added in step b),
or by modifying the pH to shift the chemical equilibria in favour or in disfavour of complexation.

For the purposes of the present invention, the expression "difference between the stoichiometric proportions and the amounts of free lanthanide and of free macrocyclic chelate added in step b)" means that the amounts of free lanthanide and of free chelate added in step b) are such that, in the light of the stoichiometry of the complexation reaction, not all the lanthanide is complexed by the chelate (excess lanthanide and/or deficit of chelate relative to the stoichiometry) or not all the chelate is complexed with the lanthanide (excess chelate and/or deficit of lanthanide).

Advantageously, this difference is such that the macrocyclic chelate/lanthanide or lanthanide/macrocyclic chelate mol/mol ratio is less than or equal to 1.4, advantageously between 1.001 and 1.3, particularly advantageously between 1.005 and 1.2, and in particular between 1.005 and 1.02. It is also pointed out that this ratio may be adapted depending on whether an excess of chelate or an excess of lanthanide is used. When an excess of lanthanide is used for the complexation, advantageously the lanthanide/macrocyclic chelate mol/mol ratio is typically less than or equal to 1.2. When an excess of chelate is used for the complexation, the macrocyclic chelate/lanthanide mol/mol ratio is advantageously less than or equal to 1.4.

Thus, in one advantageous embodiment, the amounts of free macrocyclic chelate and of free lanthanide added are such that not all the macrocyclic chelate is complexed with the lanthanide or such that not all the lanthanide is complexed with the macrocyclic chelate. Consequently, after this step b), the pharmaceutical formulation will typically comprise macrocyclic chelate-lanthanide complex and:
either free macrocyclic chelate,
or free lanthanide.

In this case, the preparation process according to the present invention is characterized in that, in step b), there is a difference between the amounts of free macrocyclic chelate and of free lanthanide added and the stoichiometric proportions, this difference advantageously being such that the macrocyclic chelate/lanthanide or lanthanide/macrocyclic chelate mol/mol ratio is less than or equal to 1.4, advantageously between 1.001 and 1.3, particularly advantageously between 1.005 and 1.2 and in particular between 1.005 and 1.02.

According to particular embodiments, the ratio will be, for example, 1.01, 1.02, 1.03 or 1.04. This gives, for example, the concentrations presented in Table 1 below, which shows the case of an excess of initial free lanthanide, given that an excess of initial chelate may also be used.

| Concentration of free macrocyclic chelate (initial) added in step b) (M) | Concentration of free lanthanide (initial) (1) added in step b) (M) | Lanthanide/chelate ratio |
|---|---|---|
| 0.480 | 0.520 | 1.083 |
| 0.487 | 0.513 | 1.053 |
| 0.492 | 0.508 | 1.032 |
| 0.497 | 0.504 | 1.014 |

(1) this is the amount of $Gd^{3+}$, and not of $Gd_2O_3$

For example, in the case of the chelate DOTA, an amount of free chelate corresponding to a concentration of 0.497 M of chelate and an amount of free lanthanide corresponding to a concentration of 0.504 M of lanthanide, which corresponds to a lanthanide/DOTA mol/mol ratio of x=1.014 (with x=0.504/0.497), will be added in step b).

Another way of expressing this difference relative to the stoichiometric proportions is to define it relative to the lanthanide concentration in the final solution.

In the case of this example which illustrates an excess of lanthanide, the difference is 0.6%=100*[(0.5−0.497)/0.5], for a formulation at 0.5 M of gadolinium at stoichiometry. The difference is thus, for example, advantageously between 0.1 mol % and 2 mol % of the concentration at stoichiometry of the pharmaceutical formulation.

In one embodiment that is also advantageous (preferred mode) the adjustment step d) is performed without touching the total amount of lanthanide present in the formulation, i.e. without adding or removing any lanthanide. In this case, only the total amount of macrocyclic chelate and/or the pH is modified.

For the purposes of the present invention, the term "total amount of lanthanide" means all the lanthanide present in free form and in complexed form.

For the purposes of the present invention, the term "total amount of macrocyclic chelate" means all the macrocyclic chelate present in free form and in complexed form.

Thus, in a first case (case A of the preferred mode), an excess of lanthanide relative to the macrocyclic chelate is added in step b); and step d) consists in adding free macrocyclic chelate.

In this case, the preparation process according to the present invention is characterized in that:
  in step b), the amounts of free macrocyclic chelate and of free lanthanide added are such that not all the lanthanide is complexed, the lanthanide/macrocyclic chelate ratio (mol/mol) advantageously being less than 1.2;
  step c) consists in solely measuring of $C_{lan\ 1}$, $C_{ch\ 1}$ typically being equal to 0 (or substantially equal to 0);
  step d) consists in adding to the formulation obtained in step b) the amount of free macrocyclic chelate necessary, firstly, to complete the complexation of the free lanthanide so as to obtain $C_{lan\ 1}=0$ and, secondly, to obtain an excess of free macrocyclic chelate $C_{ch\ 1}=C_{t\ ch\ 1}$.

In a second case (case B of the preferred mode), an excess of macrocyclic chelate relative to the lanthanide is added in step b). In this case, depending on the excess of chelate, step d) consists in adding or removing macrocyclic chelate.

Specifically, when the excess chelate added in step b) makes it possible to obtain $C_{ch\ 1}<C_{t\ ch\ 1}$, it is then appropriate in step d) to add further free macrocyclic chelate in order to obtain $C_{ch\ 1}=C_{t\ ch\ 1}$.

On the other hand, if the excess chelate added in step b) makes it possible to obtain $C_{ch\ 1}>C_{t\ ch\ 1}$, it is then appropriate in step d) to remove free macrocyclic chelate (where appropriate, to add free Gd) in order to obtain $C_{ch\ 1}=C_{t\ ch\ 1}$.

In this latter case, the preparation process according to the present invention is characterized in that:
  in step b), the amounts of free macrocyclic chelate and free lanthanide added are such that all the lanthanide is complexed and that $C_{ch\ 1}>C_{t\ ch\ 1}$, the macrocyclic chelate/lanthanide ratio (mol/mol) advantageously being less than 1.2;
  step c) consists in solely measuring $C_{ch\ 1}$, $C_{lan\ 1}$ being equal to 0;
  step d) consists in removing the appropriate amount of free macrocyclic chelate so as to obtain $C_{ch\ 1}=C_{t\ ch\ 1}$.

It is pointed out that, in cases A) and B), as illustrated in the detailed Example 2, the adjustment step d) comprises at the end a step of adjustment of the pH and of the volume, advantageously with meglumine for DOTA.

In a third case (case C) the pH of the formulation (and optionally other functionally equivalent chemical parameters) is controlled so as to shift the reaction equilibrium in order to obtain at the end the target pharmaceutical solutions (excess amount of target ligand).

According to one embodiment, the preparation process is such that:
  in step b), the amounts of free macrocyclic chelate and of free lanthanide added are equal to the stoichiometric proportions;
  it comprises between steps b) and c) an intermediate step b1) of modifying the pH of the pharmaceutical formulation obtained in step b) so as to shift the chemical equilibria in favour or in disfavour of complexation;
  step c) is performed on the formulation obtained in step b1);
  step d) consists in adjusting $C_{ch\ 1}$ and/or $C_{lan\ 1}$ so as to obtain $C_{ch\ 1}=C_{t\ ch\ 1}$ and $C_{lan\ 1}=0$ (or substantially 0) by modifying the pH so as to shift the equilibrium in the direction opposite to that of step (b1) and optionally by adding or removing free macrocyclic chelate.

For example, the process according to the invention is characterized in that:
  in step b), the mixing is performed at a pH of between 4 and 7, advantageously between 5 and 6.5,
  step b1) consists in increasing the pH using a base up to a value of between 10 and 13 and advantageously between 11 and 12,
  step d) consists in lowering the pH down to a value of between 6.5 and 7.5 and advantageously between 6.8 and 7.4, and optionally adding or removing free macrocyclic chelate.

For example, the complexation is performed at a pH below 6 (for example between 3 and 6 and advantageously between 5 and 6) and the pH is then raised, for example, to about 12 (for example with NaOH), and the pH is then adjusted to about 7.

In variants of the process without pH adjustment, as described in the detailed Example 2 of the present patent application, in step 2, the complexation is typically performed at a pH below 6 (for example between 3 and 6), the pH being brought directly to about 7. Without going into the complex mechanisms, it is indicated that, given the thermodynamic constants varying according to the pH, step b1) of the process with pH adjustment is such that it makes it possible to achieve the target range of excess free chelate in the pharmaceutical solution at least up to the expiry of the shelf life of the pharmaceutical solution. Increasing the pH makes it possible to shift the equilibrium in the direction from an excess of macrocyclic chelate to a level substantially equal to the target excess amount. Next, by reducing the pH, a reduction at a very low rate in the amount of free macrocyclic chelate is obtained such that, over the shelf life of the product, the amount of free lanthanide/macrocyclic chelate does not change unfavourably. This would result from the implied thermodynamic constants associated with the pH modifications.

It may also be pointed out that when the free lanthanide measurement will be performed (at pH 7), the concentration will be lower than if the pH change had not been made, and the adjustment is then made with the correct amount of chelate.

Furthermore, without going into the detail of the complexation mechanisms that take place at the molecular level in several phases (described especially in Chem. Eur. J., 2004, 10, 5218-5232), the Applicant points out that it was not at all obvious that the process with adjustment would make it possible to obtain this result.

In another advantageous embodiment, step b) consists in preparing a solid complex [chelate-lanthanide] and in dissolving it (in water).

In this case, step d) is performed on a liquid formulation obtained by dissolving a solid [chelate-lanthanide] complex.

According to this embodiment, step b) of the process according to the invention comprises two sub-steps:
i) the preparation of a solid complex [chelate-lanthanide] and
ii) the dissolution of the complex obtained in step i).

The adjustment in step d) may be performed as described previously in detail (addition of chelate or of lanthanide, removal of chelate or of lanthanide, adjustment by pH modification).

The preparation of the solid complex, which is advantageously crystalline [chelate-lanthanide], involves, where appropriate, at least one treatment step (filtration, concentration, crystallization, drying, spraying, etc.) for obtaining the appropriate physicochemical characteristics, especially in terms of solubility and purity.

As a conclusion, the manufacturing methods of the Applicant allow the optimized control of the proper range of free ligand excess, which is important for the clinicians. In vivo the scavenging capacity towards free gadolinium is presumably much higher for free ligand (DOTA for instance) than for excipient X[X',L] (sodium salt of DOTA-Ca for instance). Taking the example of DOTA as macrocyclic chelate, considering that the kinetic of complexation/uncomplexation of an excipient X[X',DOTA] is much less that of free DOTA, this excipient would liberate the DOTA only slowly and/or a little in physiological situation, as compared to the free DOTA. Thus free DOTA of the formulation of the applicant is, as regards to free Gd complexing, significantly more available than the DOTA of the excipient X[X', DOTA], notably in case of an accumulation of complex in a biological compartment. As a result, free DOTA excess is highly much better than excipient X[X',DOTA] for avoiding the transmetallation due to free gadolinium in vivo.

It is precised that this is different from the case of linear chelates (DTPA-BMA notably), for which the excipient X[X',L] is used because this excipient uncomplexes very quickly (or leads to quick transmetallation) and thus can scavenge free Gd. This effect of excipient X[X',L] for linear chelates has been recently demonstrated in vivo on human skin NSF patients and this excipient is added in high quantity (5 to 10% mol/mol).

In addition, in another particularly advantageous embodiment, a further technical problem was solved by the Applicant for the industrial manufacture of a pharmaceutical formulation of contrast agent based on a macrocyclic chelate-lanthanide complex, while at the same time making it possible to maximize the tolerance profile of the contrast product. More specifically, contrary to the prior-art teaching, for example U.S. Pat. No. 5,082,649 (excess of free calcium of 1 to 25%) which completes U.S. Pat. No. 5,876,695 (which uses large quantities of calcium chelate) in the pharmaceutical formulation, the Applicant has demonstrated that, in the case of the process according to the present invention, a very low amount of calcium would make it possible to ensure the industrial control of this process and to obtain a very well-tolerated product.

More specifically, the reliability of step c) of measuring the amounts of chelate and/or of lanthanide with common industrial analytical tools is markedly improved when the amount of calcium in the components used (in particular in the macrocyclic chelate, the lanthanide and the water used in step b)) is less than a very low target value of around 15 to 200 ppm. The amount of calcium (quantity of calcium) in the macrocyclic chelate used in step b) is advantageously less than 200 ppm and advantageously in the region of or less than 50 ppm and even preferably less than 15 ppm. For example, if the amount of calcium in the DOTA [active principle in the form of powder supplemented with water in step b)—see the detailed Example 2—dissolution step 1] is too high (and especially greater than 200 ppm), calcium may complex the chelate and the adjustment of the amount of free chelate will not be performed sufficiently satisfactorily.

The low amount of calcium in the pharmaceutical solution makes it possible to avoid possible disadvantageous interferences regarding the assays of free macrocyclic chelate (for example by complexing the calcium with the chelate) and thus to obtain an assay of the free chelate and its adjustment in a manner that is particularly effective for manufacture at the industrial scale at the required high level of quality. Furthermore, a very low calcium concentration controlled in the final product administered to the patient (especially the meglumine salt of gadolinium DOTA) is advantageous as regards the calcaemia of the patients in so far as it makes it possible to avoid any homeostasis imbalance: the impact of the injected product (typically at a dose of less than 20 ml) on the calcaemia is at most in the region of 0.5%. The amount of calcium in the administered contrast product is advantageously less than 50 ppm and especially less than 20 ppm, for example between 1 and 5 ppm. For example, for the meglumine salt of gadolinium DOTA, a limit of 15 µg of Ca/g of DOTA powder (15 ppm) used in step b) corresponds to 3 µg Ca/ml of liquid contrast product administered to the patient (there is about 0.202 g of DOTA per ml of administered liquid contrast product), i.e. 3 ppm in this contrast product.

The different variants of the process according to the invention as described previously thus advantageously comprise, before the measuring and adjustment steps c) and d), an intermediate step b2) of controlling the amount of calcium in the formulations obtained in step b).

Where appropriate, in particular if the amount of calcium in the final solution is greater than 15 ppm or advantageously greater than 10 ppm, this intermediate step comprises, following this control, the removal of the excess calcium.

Thus, according to one aspect, the process according to the present invention is characterized in that the amount of calcium in the liquid pharmaceutical formulation administered to the patient is less than 50 ppm, especially less than 20 ppm, and preferably less than 5 ppm, the process advantageously comprising, before step c), an intermediate step b2) of measuring the amount of calcium and, where appropriate, of removing the excess calcium.

Furthermore, the different variants of the process according to the invention as described previously advantageously comprise, before step b), control of the amount of calcium in the components used in step b), and especially in the macrocyclic chelate intended to be dissolved, in the lanthanide (typically used in oxide form), and in the water. Advantageously, the amount of calcium in these components is less than 150 ppm and preferably less than 15 ppm. Thus, according to one aspect, the process according to the present invention is characterized in that the amount of calcium in these components (typically DOTA powder, gadolinium Gd2O3 powder, water) is less than 150 ppm and preferably less than 15 ppm. According to an aspect the invention concerns a DOTA as an intermediate product (DOTA powder or DOTA in aqueous solution) containing calcium at less than 150 ppm, preferably less than 50 ppm, and preferably less than 15 ppm.

Very advantageously, the Applicant has succeeded in removing the excess calcium in the chelate (powder) used in step b), by means, in particular for DOTA, of a purification by crystallization using a water-ethanol mixture, which makes it possible to obtain an amount of calcium advantageously less than 50 ppm. The water used for step b) is also advantageously purified, where appropriate by means of a suitable treatment, for example descaling with acids to prevent any undesired amount of calcium.

A gadolinium oxide with a purity very close to 100%, substantially of 99.999%, will preferably be used in particular.

Furthermore, it will be preferred to check that the meglumine used at the end of the adjustment step d) also comprises a small amount of calcium.

The process is also advantageously such that it uses components that have extremely low amounts of metals (for example nickel and aluminium) liable to interact with the chelate, disrupting the assays. Thus, the process advantageously includes a step of checking the amount of these metals before the measuring and adjustment steps b) and/or c) and/or d).

Finally, the process according to the present invention also advantageously comprises an additional step e) of checking $C_{ch1}$ and $C_{lan1}$, irrespective of the variant described above.

The process according to the present invention is, according to one preferred embodiment, characterized in that the pharmaceutical formulation is a pharmaceutical formulation of meglumine salt of the DOTA-gadolinium complex.

The Applicant's process makes it possible to obtain the target formulations safely. This process makes it possible to solve the problem represented by the in situ complexation, in a pharmaceutical manufacturing reactor (into which is added the pharmaceutical formulation agent). Specifically, when the lanthanide is $Gd^{3+}$, meglumine will be used as formulation agent. However, given the physicochemical characteristics of gadoteric acid, the mixing of the three components (powder of non-complexed chelate, lanthanide powder and meglumine powder) in the same reactor would not be sufficiently satisfactory. Thus, the process according to the invention that allows this problem to be solved consists in engaging the complexation, measuring the difference relative to the target, and adjusting.

Overall, the Applicant's process thus makes it possible to incorporate the chelation process into the pharmaceutical production, with an advantage especially in terms of cost price and quality.

In one advantageous embodiment, an agent for blocking the free lanthanide, other than the free macrocyclic chelate, is added in step b). Advantageously, this blocking agent is a polycarboxylic acid, especially a dicarboxylic, tricarboxylic or tetracarboxylic acid, in particular a citrate or a derivative thereof.

As regards the general inventive concept of the target range of amount of free macrocyclic chelate (0.002% to 0.4%, advantageously 0.02% to 0.3% and in particular 0.025% to 0.25%), the Applicant points out that this range differs from the teaching of U.S. Pat. No. 5,876,695 illustrated in particular by its examples, at least for the following reasons.

The Applicant's target range is very narrow, and corresponds to a selection within the very broad range presented in the said document.

The formulations described in U.S. Pat. No. 5,876,695, which concern macrocyclic chelates (especially Examples 3 and 4), are formulations with salts of chelate (calcium disodium, zinc disodium DOTA) and not with free chelate. The amounts of excess salts therein are moreover very high, at least 10%. However, in the present patent application, only the free chelates are used, and not in the form of salts.

The formulations presented in U.S. Pat. No. 5,876,695, which have an amount of free chelate of about 0.1%, concern only linear chelates (DTPA), and the DTPA formulation at 0.08% described is clearly indicated as a control solution, the said document suggesting, on the contrary, the use of a much higher amount, 2% or quite probably more.

Specifically, the only test presented as regards tolerance on the use of chelates, in Table 2 and in column 6 (lines 62-67) of the said document, shows that the reduction in toxicity is markedly less favourable for an amount of linear free chelate of 0.08 mol/mol % (Formulation A for which the amount is established on the basis of the ratio between 0.5 mmol Gd DTPA and 0.0004 mmol DTPA/kg), in comparison with the 2% amount corresponding to the advantageous formulation (Formulation B for which the amount established on the basis of the ratio between 0.5 mmol Gd DTPA and 0.01 mmol DTPA/kg) and which is described as a low value (column 6, line 61).

The Applicant thus worked on formulations with an amount of free macrocyclic chelate about 5 to 100 times lower than that explicitly recommended by document U.S. Pat. No. 5,876,695. It was thus demonstrated by the Applicant, surprisingly, that macrocyclic chelates, and more especially DOTA, behave differently from linear chelates such as DTPA as regards tolerance, resulting from the presence of an excess of free chelate.

More specifically, whereas the tolerance appears to be improved with DTPA by increasing the excess free chelate from 0.08% to 2%, the tolerance degrades, in contrast, for DOTA by increasing the excess free chelate, passing from very low values (0.025% to 0.25%) to a value of 2%. Consequently, the transposition of values to reduce the risk of toxicity, between a linear chelate (in particular DTPA), and macrocyclic chelates (in particular DOTA), is not at all obvious. This is moreover what is illustrated by the current complex discussions in the scientific community in the context of NSFs with regard to the tens of millions of doses of contrast agents already injected in man, discussions on the subject of the complexation kinetics and/or on comparisons of structures between chelates. For instance it has recently been shown that in order to reduce the risk of NSF (results on human skin where gadolinium accumulates) for some linear chelates, it is highly recommended to use very high quantities of excipient X,X'L for linear chelates, namely about 5 to 10% of such excipient, and that free chelate such as DTPA-BMA should clearly not be used.

To this end, according to another aspect, the invention relates to a pharmaceutical formulation that may be obtained via the process according to the present invention, characterized in that it contains between 0.002 and 0.4 mol/mol %, more especially between 0.02 and 0.3 mol/mol % and very advantageously between 0.025 and 0.25 mol/mol %, of free macrocyclic chelate, advantageously of free DOTA.

By virtue of the adopted selection of the range of excess free macrocyclic chelate, in particular of free DOTA, a value of free lanthanide in solution, and in particular of gadolinium, of about from $10^{-10}$ M to $10^{-14}$ M at physiological pH, is obtained.

The concentration of complexed chelate in the formulation is typically between 1 µM and 1 M, with an administered dose of about from 0.01 to 5 mmol/kg. The concentration of the injected formulation is typically about 0.5 M.

The process particularly advantageously relates to the preparation of the pharmaceutical formulation of the meglumine salt of the DOTA-gadolinium complex: the macrocyclic chelate and the free macrocyclic chelate are DOTA, the lanthanide is gadolinium, and the prepared salt is the meglumine salt.

Advantageously, the pharmaceutical formulation according to the present invention is characterized in that the macrocyclic chelate is DOTA and in that the formulation contains between 0.02 and 0.08 mol/mol % of free DOTA.

This lower range is liable to have several physiological advantages:
- limiting a risk of chelation for certain diseases of endogenous cations (for example zinc or copper) by the presence of an overly large excess of macrocyclic chelate,
- limiting the inhibition of metalloenzymes, especially ACE, with an impact on the regulation of arterial hypertension, for example,
- avoiding unfavourable medicinal interactions with metallic active principles: lithium, bismuth, platinum, etc.,
- avoiding disrupting the seric dosages of endogenous metals,
- avoiding medicinal interactions with active principles that are complexing, for example detoxifying (deferroxamine, cyclam, etc.).

In another advantageous embodiment, the pharmaceutical formulation according to the present invention is characterized in that the macrocyclic chelate is DOTA and in that the formulation contains between 0.15 and 0.25 mol/mol % of an excess amount of free DOTA.

This higher range is liable to have several physiological advantages:
- optimally limiting the amount of free gadolinium injected, the free gadolinium being a toxicity risk and possibly being involved in phagocytosis mechanisms associated with certain diseases,
- minimizing the in vivo transmetallation in pathological situations, especially transmetallation by iron (increase in seric iron).

This higher range is also an advantage for further improving the stability of the formulation to be injected over time (dechelation under unsuitable storage conditions: heat, depressurization in aircraft, excessive exposure to light, etc.).

According to one embodiment, the amount of free macrocyclic chelate is between 0.09% and 0.15%. This median range is liable to combine advantages of the lower and higher ranges.

The choice of the amount of free macrocyclic chelate may be optimized in particular as a function of the risk of the patients for various pathologies or pathological risks associated with the mechanisms presented hereinabove. For example, in the case of patients presenting a risk of NSF, an excess of macrocyclic chelate in the median or high range may be preferred, to minimize any release of gadolinium.

Very low values of excess free chelate are, however, also liable to have a beneficial effect in the pathology NSF if it turns out in certain categories of patients (kidney failure patients in particular) that this pathology is partly associated with a presence of free chelate, which would involve in vivo transmetallation or similar phenomena that are unfavourable in terms of tolerance.

According to another aspect, the calcium content of the pharmaceutical formulation (administered to the patient) according to the invention is less than 50 ppm, advantageously less than 30 ppm and advantageously less than 15 ppm.

According to another aspect, the invention relates to use of a contrast product formulation, the said formulation comprising a complex of macrocyclic chelate with a paramagnetic metal ion and an amount of free macrocyclic chelate of between 0.025% and 0.25%, advantageously of a formulation according to the present invention, for improvement of the tolerance.

According to another aspect, the invention relates to a method for improving the in vivo tolerance of an MRI contrast product based on macrocyclic chelate, and more especially on DOTA, which consists in using an excess of free chelate in an amount of between 0.025 and 0.25 mol/mol %, especially 0.025-0.08%, 0.09-0.15%, 0.16-0.25%.

Advantageously, the concentration of chelate (complexed chelate) in the formulation is between 0.5 and 0.9 M.

The macrocyclic chelate that is useful in the context of the present invention is advantageously chosen from the following chelates: DOTA, NOTA, DO3A, BT-DO3A, HPDO3A, PCTA, DOTAGA and derivatives thereof, and is most particularly DOTA. The chemical formulae of these chelates are widely known to those skilled in the art, and are recalled, for example, in WO 2007/042 504, on pages 20 to 23, and WO 2003/011 115, on pages 8 to 11.

The invention also relates to the use of a pharmaceutical formulation according to the invention for the preparation of a diagnostic composition for medical imaging, or for diagnostic monitoring of the efficacy of a therapeutic treatment, and to a diagnostic method comprising the administration of a pharmaceutically acceptable amount of a formulation according to the invention.

For diagnosis in MRI, the intravenous administration by injection usually as a saline solution is typically performed at a dose of from 1 to 500 µmol Gd/kg. The pharmaceutically acceptable unit doses will depend on the nature of the chelate, the route of administration, and on the patient and especially on the nature of the disorder to be studied. For an intravenous injection and observation by magnetic resonance, the concentration of the solution will typically be between 0.001 and 0.5 mol/liter, and from 0.001 to 0.1 millimol/kg will be administered to the patient, depending on the case. Higher clinical doses may also be practised, for example a triple dose (0.3 millimol/kg). The administration rate, the concentration, the speed of injection are adapted according to the clinical indication and product specifications, and eventually also in view of the behaviour of the contrast agent during the MRI procedure. Any appropriate protocol is used, with possible adjustment of the administration in view of the patient data, of first test injections operated, of the enhancement curves obtained. The speed of injection may be calculated (advantageously automatically by data treatment tools) according to the protocol and during the protocol in view of the relaxivity curve during the course of the acquisition; for instance if the administration rate/speed is not sufficient for optimal enhancement considering the data base, the injector automatically increases this rate during the MRI procedure.

Among the advantageous diagnostic indications, mention will be made of the indications already used clinically, and the indications for which the results are improved by virtue of the formulations according to the invention. Mention will thus be made of the following indications and improvements thereof: angiography, cerebral imaging, vascular imaging, imaging of cardiovascular, cancer, neurodegenerative and inflammatory pathologies, any indication with perfusion imaging, any indication combining the use of several contrast products, especially MRI, X-ray scanner, SPECT, PET, PET CT, and any indication with successive administrations of contrast products at the same or at different concentrations, or in multimodal imaging.

According to embodiments, these novel formulations may be chosen to be administered in combination with or in place of prior-art formulations as a function of the diagnostic profile of the patient, and especially of the profile of tolerance of the patient to the contrast products. The choice may be made by the practician and/or automatically by any tagging system (RFID tag carried by the patient, . . . ) and conditioning the type of administration, for example the choice of the contrast agent best adapted such as the formulation of the present application.

An installation comprising a device for evaluating the tolerance of the patient, and a device like an injector for administering the formulation of the contrast product as a function of the result given by the evaluation device may thus be used. Several risks may be evaluated, especially the risk of NSF (nephrogenic fibrosis). Where appropriate, the MRI product is co-administered simultaneously with or subsequently to at least one anti-NSF therapeutic agent (anti-fibrosis agent known therapeutically, especially steroids, anti-inflammatories or vitamins, for example).

Where appropriate, an evaluation of the patient's risk with respect to NSF is performed to optimize the dose/concentration of injected contrast product (for example, the dose may be reduced relative to the common clinical dose, if it makes it possible, while avoiding any risk, to obtain sufficiently satisfactory information to obtain the signal in imaging).

To further reduce the risk of toxicity of the lanthanide in the case of at-risk patients, the Applicant also studied formulations comprising:
- as in the prior art: the chelate of lanthanide (for example gadoteric acid DOTA-Gd complex or a linear Gd-chelate) and the salification agent for neutralizing the chelate, for example meglumine (organic base),
- but in addition with at least one biocompatible supplementary excess blocking agent, intended to block any lanthanide ($Gd^{3+}$) that might otherwise remain free in the formulation.

Among the blocking agents that will especially be used are organic anions such as monocarboxylic or polycarboxylic acids (advantageously tricarboxylic or tetracarboxylic, such as citrate and derivatives thereof), hydroxy acids (lactate, malate . . . ), or other agents capable of an advantageous coordination interaction with the lanthanide.

The blocking agent may thus be introduced into the formulation and/or co-administered to the patient.

DETAILED EXAMPLES

1) Example 1

In Vivo Tolerance

The tolerance results in Table 2 (acute toxicity in mice for a diagnostic solution of DOTA; this solution is a pharmaceutical solution injected and comprising the complex of DOTA with the Gd3+, and an excess of free DOTA not complexed by Gd3+ and not complexed by metal ions as excipient) show that formulations containing from 0.025 to 0.25 mol/mol % of free macrocyclic chelate DOTA are three times less toxic than the formulation close to 2%.

| Test | Excess of Free DOTA mol/mol % | Male $LD_{50}$ Mmol/kg | Female $LD_{50}$ Mmol/kg |
|---|---|---|---|
| 1 | 0.05 | 12.41 | 13.59 |
| 2 | 0.09 | 13.06 | 13.50 |
| 3 | 0.25 | 12.02 | 12.07 |
| 4 | 1.98 | 4.80 | 4.80 |

Further stability studies performed by the Applicant show that the formulations are very satisfying with no release of gadolinium for a long conservation time.

Example 2

Process for Preparing Formulations of Lanthanide Chelate (Mixture of a Solution of Chelate and of a Solution of Lanthanide)

The preparation of formulations in which the macrocyclic chelate is DOTA is more specifically described. Table 3 below gives an example of the amounts used for the manufacture of a solution of 100 liters of DOTA (industrial amount).

| Component | Amount |
|---|---|
| DOTA (1) | 20.100 kg (i.e. 0.497M) |
| Gadolinium oxide (expressed as anhydrous product) | 9.135 kg (i.e. 0.504M) |
| Meglumine (expressed as anhydrous product) | 9.215 kg |
| Solution for adjusting DOTA to 5% qs amount of free DOTA 3N meglumine solution qs pH = 6.8-7.4 at 20° C. | 15-35 mg per 100 ml |
| Injection-grade water qs | 100 litres |

(1) 1,4,7,10-Tetraazacyclododecane-N,N',N'',N'''-tetraacetic acid

Step 1: Dissolution 40 liters of injection-grade water at 80° C. are placed in a 100-liter manufacturing tank, the injection of nitrogen is started, and the 20.100 kg of DOTA and the 9.135 kg of gadolinium oxide are then incorporated with stirring. The complexation is performed at a pH below 6, for example between 3 and 6, for example at pH 4. The gadolinium oxide in the presence of DOTA forms a water-soluble acid complex.

Step 2: Measurements

After step 1, a sample is taken and the free gadolinium is assayed.

Step 3: Adjustment of the Free Species

The adjustment of the solution is advantageously performed with gadolinium oxide or DOTA.

A DOTA-adjusting solution is thus added qs an amount of 15-35 mg per 100 ml.

Step 4: Cooling

The final solution from step 3 is cooled to 30° C., for example by circulating cold water in the tank jacket.

Step 5: Adjustment of the pH and of the Mass Per Unit Volume

The acid function of the complex formed is salified with meglumine and the pH at 20° C. is adjusted to 6.8-7.4. The concentration is adjusted by adding injection-grade water.

The following are thus introduced into the manufacturing tank:

9.125 kg of meglumine and a solution of meglumine pH=6.8-7.4 at 3N injection-grade water, qs.

The final solution is then filtered and then placed in bottles typically sterilized by autoclaving.

2) Example 3

Process for Preparing Formulations of Lanthanide Chelate (Dissolution of a Solid Complex [Chelate-Lanthanide])

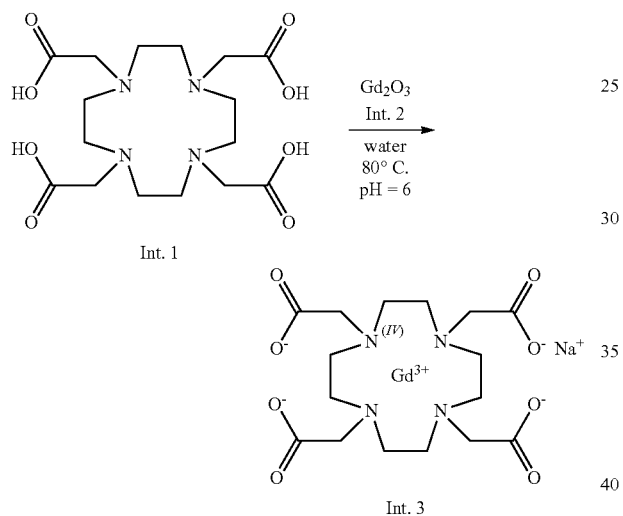

This example illustrates the manufacture of a small amount of product, the appropriate transposition being performed at the industrial scale.

|  | Int. 1 | Int. 2 ($Gd_2O_3$) | Int. 3 |
|---|---|---|---|
| $M_w$ (g · $mol^{-1}$) | 404.42 | 362.70 | 580.63 |
| m (g) | 10 | 4.48 |  |
| n (mol) | 0.025 (1 Eq) | 0.0125 (0.5 Eq) |  |

10 g (0.025 mol; 1 eq) of macrocyclic chelate DOTA are dissolved in 200 ml of water by heating to 80° C., in a three-necked flask equipped with a condenser, a thermometer and a pH meter. The measured pH is 3.7. It is adjusted to 6 with 2N NaOH solution. 4.48 g (0.0125 mol; 0.5 eq) of gadolinium oxide are added. The pH is readjusted and kept stable at between 6 and 7 by adding 1N HCl. The reaction is left at 80° C. with stirring.

The residual free gadolinium is removed by means of a chelex resin prerinsed with water. To do this, the reaction mixture is brought to pH 5 (the resin is more efficient). The whole is left for 2 hours with stirring at room temperature. The pH rises to between 6.5 and 7. The resin is removed by filtration.

The complex is precipitated in ethanol to remove the salts (5 volumes of EtOH per 1 volume of water).

An assay of the salts is performed by titration with a 0.05N silver nitrate solution. Quantification of the free gadolinium is also performed by colorimetric assay with Arsenazo (III). 11.5 g of product are obtained (white powder).

Yield=80%; HPLC purity: 98%; LC/MS ($ES^+$ mode): z=1 (m/z=559).

The dissolution in water is then performed via suitable methods, for example using a water at 45° C., with stirring for about 30 minutes, and with adjustment of the pH.

The invention covers broadly other embodiments deriving from the ones presented in detail. For instance the meglumine is added to a solution of DOTA and afterwards gadolinium is added for the step of DOTA complexation by gadolinium.

The invention claimed is:

1. An industrial process for preparing a liquid pharmaceutical formulation containing a complex of macrocyclic chelate with a lanthanide and a mol/mol amount of free macrocyclic chelate of between 0.002% and 0.4%, wherein the process comprises the following successive steps:
    (b) preparing a liquid pharmaceutical formulation containing a complex of macrocyclic chelate with a lanthanide, and:
    free lanthanide,
    and optionally free macrocyclic chelate;
    said step (b) consisting of mixing a solution of free macrocyclic chelate and free lanthanide wherein the lanthanide/macrocyclic chelate mol/mol ratio is between 1.001 and 1.3;
    (c1) adjusting the pH of a sample of the liquid pharmaceutical formulation obtained in step (b) so that the concentration of free macrocyclic chelate $C_{ch\ 1}$ is equal to 0;
    (c2) measuring in the sample of the liquid pharmaceutical formulation obtained in step (c1) the concentration of free lanthanide $C_{lan\ 1}$;
    (d) adjusting the concentration of free macrocyclic chelate $C_{ch\ 1}$ in the liquid pharmaceutical formulation based on the measurements obtained in step (c2) by adding to the formulation obtained in step (b) the amount of free macrocyclic chelate necessary to complete the complexation of the free lanthanide so as to obtain $C_{lan\ 1}$=0, and to obtain $C_{ch\ 1}$=$C_{t\ ch\ 1}$, wherein $C_{t\ ch\ 1}$ is the target concentration of the free macrocyclic chelate in the final liquid pharmaceutical formulation and is between 0.002% and 0.4%, and adjusting the pH of the final liquid pharmaceutical formulation with meglumine;
    wherein the amount of free macrocyclic chelate in the final liquid pharmaceutical formulation corresponds to the proportion of free macrocyclic chelate relative to the amount of complexed macrocyclic chelate in the final liquid pharmaceutical formulation;
    wherein the complex of macrocyclic chelate with a lanthanide is the meglumine salt of the DOTA-gadolinium complex, the macrocyclic chelate is DOTA and the lanthanide is gadolinium;
    wherein the operating steps (b) and (d) of the process occur in the same reactor; and
    wherein the liquid pharmaceutical formulation is an injectable solution.

2. Process according to claim 1, wherein any calcium present in the final liquid pharmaceutical formulation is present in an amount of less than 50 ppm.

3. Process according to claim 2, wherein the amount of calcium present in the final liquid pharmaceutical formulation is less than 20 ppm.

4. Process according to claim 3, wherein the amount of calcium present in the final liquid pharmaceutical formulation is less than 5 ppm.

5. Process according to claim 2, wherein the liquid pharmaceutical formulation is prepared from ingredients including chelate powder, water and meglumine, and wherein the amount of calcium in the ingredients used to prepare the final liquid pharmaceutical formulation is less than 50 ppm.

6. Process according to claim 2, wherein it comprises, before step (c1), an intermediate step (b2) of measuring the amount of calcium in the obtained solution, and removing any excess calcium in order to obtain an amount of less than 50 ppm in said solution.

7. Process according to claim 1, further comprising as step (e) the step of checking concentrations $C_{ch\ 1}$ and $C_{lan\ 1}$ after step (d).

8. Process according to claim 1, wherein the mol/mol amount of free macrocyclic chelate is between 0.025% and 0.25%.

9. Process according to claim 1, wherein step (b) is carried out at a temperature of between 60° C. and 100° C.

10. The process of claim 1, wherein gadolinium is added as gadolinium oxide in step (b).

11. The process of claim 1, wherein said step (b) consists of mixing a solution of free macrocyclic chelate and free lanthanide for 1 to 3 hours at a pH of between 4 and 7.

12. The process of claim 1, wherein step (d) comprises adjusting the pH of the final liquid pharmaceutical formulation with meglumine to between 6.5 and 7.5.

13. An industrial process for preparing a liquid pharmaceutical formulation containing a complex of macrocyclic chelate with a lanthanide and a mol/mol amount of free macrocyclic chelate of between 0.002% and 0.4%, wherein the process comprises the following successive steps:

(b) preparing a liquid pharmaceutical formulation containing a complex of macrocyclic chelate with a lanthanide, and:

free lanthanide, and optionally free macrocyclic chelate;

said step (b) consisting of mixing a solution of free macrocyclic chelate and free lanthanide for 1 to 3 hours at a temperature between 60° C. and 100° C. at a pH between 4 and 7 wherein the lanthanide/macrocyclic chelate mol/mol ratio is between 1.001 and 1.3;

(c1) adjusting the pH of a sample of the liquid pharmaceutical formulation obtained in step (b) to 7;

(c2) measuring in the sample of the liquid pharmaceutical formulation obtained in step (c1) the concentration of free lanthanide $C_{lan\ 1}$;

(d) adjusting the concentration of free macrocyclic chelate $C_{ch\ 1}$ in the liquid pharmaceutical formulation based on the measurements obtained in step (c2) by adding to the formulation obtained in step (b) the amount of free macrocyclic chelate necessary to complete the complexation of the free lanthanide so as to obtain $C_{lan\ 1}=0$, and to obtain $C_{ch\ 1}=C_{t\ ch\ 1}$, wherein $C_{t\ ch\ 1}$ is the target concentration of the free macrocyclic chelate in the final liquid pharmaceutical formulation and is between 0.002% and 0.4%, and adjusting the pH of the final liquid pharmaceutical formulation with meglumine to between 6.5 and 7.5;

wherein the amount of free macrocyclic chelate in the final liquid pharmaceutical formulation corresponds to the proportion of free macrocyclic chelate relative to the amount of complexed macrocyclic chelate in the final liquid pharmaceutical formulation;

wherein the complex of macrocyclic chelate with a lanthanide is the meglumine salt of the DOTA-gadolinium complex, the macrocyclic chelate is DOTA and the lanthanide is gadolinium; and wherein the operating steps (b) and (d) of the process occur in the same reactor.

14. The process of claim 1, wherein in step (c1), the pH is adjusted to 7.

* * * * *

UNITED STATES PATENT AND TRADEMARK OFFICE
CERTIFICATE OF CORRECTION

PATENT NO. : 9,655,983 B2
APPLICATION NO. : 12/918259
DATED : May 23, 2017
INVENTOR(S) : Dominique Meyer et al.

Page 1 of 1

It is certified that error appears in the above-identified patent and that said Letters Patent is hereby corrected as shown below:

In the Specification

Column 5, Line 38, in Step 1, change:
"$[L]_{initial} + [lan]_{initial} \rightarrow [L\text{-}lan] + [L]_{free}$ or $[lan]_{free}$"
To:
-- $[L]_{initial} + [lan]_{initial} \rightarrow [L\text{-}lan]_{initial} + [L]_{free}$ or $[lan]_{free}$ --.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*